United States Patent
Koehl et al.

(10) Patent No.: US 11,122,800 B2
(45) Date of Patent: Sep. 21, 2021

(54) ANTIMICROBIAL ORGANIC PRESERVATIVES

(71) Applicant: Troy Corporation, Forham Park, NJ (US)

(72) Inventors: David Joseph Koehl, Bethlehem, PA (US); Brian Joseph Mullaney, Poughkeepsie, NY (US)

(73) Assignee: Troy Corporation, Florham Park, NJ (US)

( * ) Notice: Subject to any disclaimer, the term of this patent is extended or adjusted under 35 U.S.C. 154(b) by 0 days.

(21) Appl. No.: 15/799,998

(22) Filed: Oct. 31, 2017

(65) Prior Publication Data

US 2019/0124921 A1 May 2, 2019

Related U.S. Application Data (60) Provisional application No. 62/579,081, filed on Oct. 30, 2017.

(51) Int. Cl.
| | |
|---|---|
| *A01N 37/02* | (2006.01) |
| *A61P 31/04* | (2006.01) |
| *A61P 31/00* | (2006.01) |
| *A01N 37/10* | (2006.01) |
| *A01N 37/06* | (2006.01) |
| *A01N 31/14* | (2006.01) |
| *A61Q 19/00* | (2006.01) |
| *A61K 8/365* | (2006.01) |
| *A61K 8/368* | (2006.01) |
| *A61K 8/36* | (2006.01) |
| *A61K 8/34* | (2006.01) |
| *A61Q 5/02* | (2006.01) |
| *A01N 31/04* | (2006.01) |
| *A01N 37/42* | (2006.01) |
| *A61Q 17/00* | (2006.01) |

(52) U.S. Cl.
CPC ............ *A01N 37/02* (2013.01); *A01N 31/04* (2013.01); *A01N 31/14* (2013.01); *A01N 37/06* (2013.01); *A01N 37/10* (2013.01); *A01N 37/42* (2013.01); *A61K 8/34* (2013.01); *A61K 8/347* (2013.01); *A61K 8/36* (2013.01); *A61K 8/365* (2013.01); *A61K 8/368* (2013.01); *A61P 31/00* (2018.01); *A61P 31/04* (2018.01); *A61Q 5/02* (2013.01); *A61Q 17/005* (2013.01); *A61Q 19/00* (2013.01); *A61Q 19/007* (2013.01); *A61K 2800/524* (2013.01)

(58) Field of Classification Search
CPC ........ A01N 31/04; A01N 31/14; A01N 37/02; A01N 37/06; A01N 37/42; A61P 31/00; A61P 31/04; A61Q 5/02; A61Q 17/005; A61Q 19/00; A61Q 19/007
See application file for complete search history.

(56) References Cited

U.S. PATENT DOCUMENTS

| | | | | |
|---|---|---|---|---|
| 3,623,884 A | * | 11/1971 | Haas | A23L 3/3508 |
| | | | | 426/332 |
| 2014/0275255 A1 | * | 9/2014 | Pedersen | A61K 31/19 |
| | | | | 514/558 |
| 2016/0015031 A1 | | 1/2016 | Pesaro et al. | |
| 2016/0100574 A1 | | 4/2016 | Pesaro et al. | |
| 2016/0220568 A1 | * | 8/2016 | Kanyo | A61K 31/519 |

FOREIGN PATENT DOCUMENTS

| | | | |
|---|---|---|---|
| DE | 102011088962 A1 * | 6/2013 | ............ A61K 31/19 |
| RU | 2265381 C2 * | 12/2005 | |
| WO | 2013092457 A2 | 6/2013 | |
| WO | WO-2016084078 A1 * | 6/2016 | ............ A61Q 19/00 |
| WO | 2016146778 A1 | 9/2016 | |
| WO | 2017129338 A1 | 8/2017 | |

OTHER PUBLICATIONS

Liewen, M.B., et al., "Growth and Inhibition of Microorganisms in the Presence of Sorbic Acid: A Review," Apr. 1985, vol. 48(4), pp. 364-375, Journal of Food Protection.
International Search Report and Written Opinion for International Application No. PCT/US18/58172, dated Jan. 18, 2019, 10 pages.
International Preliminary Report on Patentability for International Application No. PCT/US2018/058172, dated May 5, 2020, 8 pages.
Thiemann, A., et al., "The formulator's guide to safe cosmetic preservation", Nov. 30, 2014, pp. 39-43, XP055575562, Personal Care.
Foxon-Hill, A., "Preservative adventures with sodium levulinate and sodium anisate," Oct. 2, 2016, pp. 1-8, XP055818536.
Extended European Search Report for European Application No. 18 872 623.6, dated Jul. 8, 2021, 8 pages.

* cited by examiner

*Primary Examiner* — Theodore R. Howell
*Assistant Examiner* — George W Kosturko
(74) *Attorney, Agent, or Firm* — RatnerPrestia (57) ABSTRACT

The invention is a chemically and physically stable solution of levulinic acid, benzoic acid, and sorbic acids or their salts which is antimicrobially effective against bacteria and fungi. The solution provides improved antibacterial protection for personal care and cosmetic products at lower than expected levulinic acid levels and at desirable use levels.

The composition may also include a solvent selected from the group of aromatic alcohols consisting of phenoxyethanol, phenylpropanol, phenylethanol, benzyl alcohol, and mixtures of these alcohols. These solvents extend the range of acidity over which the invention is capable of inhibiting bacterial and fungal growth.

18 Claims, 2 Drawing Sheets

ANTIMICROBIAL ORGANIC PRESERVATIVES

CROSS-REFERENCE TO RELATED APPLICATIONS

This application claims priority of a provisional application entitled "ANTIMICROBIAL ORGANIC PRESERVATIVES", which is application No. 62/579,081 filed Oct. 30, 2017, and is hereby incorporated by reference in its entirety.

BACKGROUND OF THE INVENTION

Field of the Invention

The invention relates to surprisingly effective antimicrobial compositions for protecting personal care products against degradation associated with bacterial and fungicidal growth.

Background of the Invention

Personal care and cosmetic products typically contain ingredients that can support the growth of bacteria and fungi. If left unchecked, bacteria and fungi can degrade these personal care and cosmetic products or pose a danger to the user.

Bacteria that cause this degradation include *Pseudomonas aeruginosa, Escherichia coli, Enterobacter aerogenes, Alcaligenes faecalis,* and *Staphylococcus aureus,* among others. Degrading fungi include *Aspergillus niger,* and *Penicillium* sp.

Bacterial and fungal growth may produce, among other things, discoloration, decomposition, offensive odors, phase separation, and changes in viscosity or pH values. If bacteria or fungi are allowed to flourish, they can pose a danger to end users whose immune systems are compromised or who use the products in high risk areas, such as around the eyes.

Protection against bacterial and fungal growth is often required over a relatively long period of time to protect products throughout their life cycle which includes manufacturing, storage, and extended periods after purchase by the user.

As the industry moves more and more towards naturally sourced and processed ingredients, the challenge to effectively preserve these formulations has increased. At the same time, there is a decrease in the number of approved or acceptable preservatives from which formulators can choose. Regulatory bodies in several key markets have either restricted or prohibited the use of many traditional preservatives from personal care and cosmetic products.

Additionally, traditional preservatives are highly scrutinized due to a perception amongst some consumers that "modern chemicals" are dangerous. These perceptions, often based on bad or misinterpreted science have been amplified through the use of social media and the internet. All of these forces are making it more challenging to find preservative systems that are effective, approved and acceptable to the broadest segment of consumers possible.

Unlike many traditional preservatives, organic acids have been widely accepted by consumers and industry. Benzoic acid (also known as benzenecarboxylic acid) and sorbic acid (also known 2,4-hexadienoic acid) have been used for many years to provide antifungal protection for a wide range of personal care and cosmetic products. The popularity of benzoic acid and sorbic acid has increased because they are viewed as more natural (both of these organic acids are found in nature) and because they are well known as food preservatives.

The primary weaknesses of organic acids are that they i) do not perform well against bacteria, and ii) do not perform well in alkaline or neutral environments. Organic acids are primarily effective against fungi and are usually combined with another bactericide in order to provide broad spectrum protection against bacteria and fungi. Furthermore, organic acids generally exhibit significantly decreasing efficacy as pH increases. While the upper pH limits for individual organic acids differ somewhat, the upper limit is generally in the range of about 5 to about 5.5 pH.

Low use level is a crucial characteristic for preservatives. A preservative composition that is effective at a lower use level is a superior product, as compared to other antimicrobial compositions. For the present purposes, "use level" means the proportion by weight of a component or a composition present in a in a sample or product that is intended for testing or use. Ideally, these superior compositions should protect against a wide variety of problem microorganisms and remain effective for an extended period of time, without adversely affecting the product to be protected, the health of people who make or use the product, or the environment.

Because personal care and cosmetic products vary widely in their final pH values, efficacy over a wide range of pH is also a crucial characteristic for personal care and cosmetic preservatives. A preservative that is effective across a wider range of pH is a superior product, as compared to antimicrobial compositions that exhibit a narrower effective pH range. While most organic acid preservatives are presently limited to an upper effective pH of about 5 to 5.5, a new preservative composition that allows organic acids to be utilized effectively at higher pH levels would be welcomed by the personal care and cosmetic industries.

Chemical stability, toxicological profile, regulatory considerations, environmental concerns, physical properties or other characteristics may render a particular ingredient unsuitable for a particular use. Accordingly, there is a need to constantly develop new antimicrobial compositions that offer broad spectrum protection for a variety of needs.

U.S. Pat. No. 3,793,210, issued to Garland George Corey and assigned to Colgate-Palmolive Company, describes shampoo compositions which contain ampholytic, nonionic, cationic and/or anionic surfactants and a keto acid such as levulinic acid. The Corey patent reports that these shampoo compositions produce more foam during use and provide desirable conditioning, softening and cleaning characteristics for hair. Other than stating that conventional additives such as preservatives may be included in accordance with conventional compounding practice, the Corey patent is silent on the subject of antimicrobial protection for shampoo or other personal care products.

United States Patent Application Publication No. 2016/0015031 A1, lists Manuel Pesaro et al. as inventors and is assigned to Symrise AG. The Pesaro et al. patent application describes an antimicrobial composition including at least one acetophenone derivative of specified formula; at least one second antimicrobial agent selected from a group of preservatives and their mixtures which includes (among many others) benzoic acid and its esters and salts, sorbic acid and its salts, levulinic acid and its salts, and mixtures thereof; and/or at least one antimicrobial second agent selected from a specified group of alcohols and mixtures thereof which includes phenoxyethanol. The Pesaro et al. publication does not suggest that combinations benzoic acid or its esters or salts, sorbic acid or its salts, levulinic acid and its salts, or phenoxyethanol in certain proportions may be particularly effective against bacteria or fungi.

SUMMARY OF THE INVENTION

The invention is a chemically and physically stable solution of organic acids or their salts which is antimicrobially effective against bacteria and fungi. The invention provides improved antibacterial protection for personal care and cosmetic products.

In a preferred aspect, the invention is an antifungal and antibacterial composition, which includes levulinic acid or a levulinic acid salt, about 0.1% to about 40% benzoic acid or a benzoic acid salt, and about 0.1% to about 20% sorbic acid or a sorbic acid salt. The composition may include an aromatic alcohol, such phenoxyethanol, phenylpropanol, phenylethanol, benzyl alcohol, and mixtures thereof. The composition inhibits the growth of bacteria in contact with the composition in a range of about 1.0 to about 7.0 pH and in a range of use level of about 0.2 to about 2.0%.

In another preferred aspect, the invention is an antifungal and antibacterial composition, which includes levulinic acid or a levulinic acid salt, about 0.1% to about 70% benzoic acid or a benzoic acid salt, and about 0.1% to about 20% sorbic acid or a sorbic acid salt. The composition may include an aromatic alcohol selected from the group consisting of phenoxyethanol, phenylpropanol, phenylethanol, benzyl alcohol, and mixtures thereof.

In other preferred aspects, the invention is a personal care product or a cosmetic product that includes the inventive antifungal and antibacterial composition. The personal care product or the cosmetic product may have an acidity in the range about 1.0 to about 7.0 pH.

These and other aspects of the invention are described below.

DETAILED DESCRIPTION OF PREFERRED EMBODIMENTS

In a preferred embodiment, the invention is a chemically and physically stable solution of levulinic acid, benzoic acid, and sorbic acid or the respective salts of these organic acids, which is effective as an antimicrobial against bacteria and fungi. Examples of the salts of these organic acids include sodium levulinate, calcium levulinate, magnesium levulinate, sodium benzoate, calcium benzoate, magnesium benzoate, calcium sorbate, sodium sorbate, and potassium sorbate. Levulinic acid (also known as 4-oxopentanoic acid) is somewhat unusual among organic acids in that it has greater efficacy against bacteria than against fungi. In contrast, most organic acids are primarily effective against fungi.

To create a new and improved composition that is effective against a broad spectrum of microbes, the present invention utilizes levulinic acid combined with benzoic acid and sorbic acid. Surprisingly, the addition of small amounts of sorbic acid to levulinic acid and benzoic acid results in greatly improved antibacterial efficacy, even at significantly lower levels of levulinic acid. Improvement in antibacterial efficacy is demonstrated below in Tables 4 and 6 of the Examples. Table 10 below reports an improvement in Minimum Inhibitory Concentration against bacteria and fungi that is associated with a greater proportion of sorbic acid in certain mixtures of levulinic acid, benzoic acid and sorbic acid.

For the present purposes, "personal care and cosmetic products" means products adapted for use in hair care, skin care, oral care, toiletries, deodorants, grooming, sun care, baby care, color cosmetics, and wet wipes.

In order to be accepted by the personal care and cosmetic industries, a broad spectrum preservative blend must be chemically and physically stable, as well as biologically active. Earlier researchers reported that levulinic acid decomposes in the presence of water and certain alcohols. Shu, C.-K.; Lawrence, B. M., *Formation of 4-alkoxy-γ-valerolactones from levulinic acid and alcohols during storage at room temperature*, J. Agric. Food Chem., 1995, 43, 3, 782-784.

The inventors were pleasantly surprised to discover that some aromatic alcohols, such as phenyl propanol, benzyl alcohol and phenoxyethanol, are stable in the presence of levulinic acid. This is an important discovery, because stable solvent systems broaden the range over which levulinic acid—benzoic acid—sorbic acid solutions may be formulated into a stable liquid solution. With this flexibility, the antimicrobial composition of the invention is useful as a preservative for a wider range of personal care product such as shampoos, wet wipes, body lotions and other applications. The data in FIG. 1 and FIG. 2 indicates that mixtures of levulinic acid with phenoxyethanol and phenylpropanol, respectively, are sufficiently stable.

Examples of specific cosmetic and personal care end-use formulations which can be protected by the invention include shampoos, conditioners, styling gels, body creams and lotions, anti-aging & anti-wrinkle creams, anti-cellulite creams, intimate care products, personal lubricants, self-tanning products, whitening products, facial mask (peel off), body wash, shower scrubs, liquid hand soap, bar soap, lip gloss, lip stick, toothpaste, mouth wash, perfumes, deodorants, antiperspirants, shaving creams and gels, talcum powder, sun screens, nail polish, press powders, eye and facial makeup, baby wipes, makeup removal wipes, facial mask (pre-moistened nonwoven), personal cleansing wipes, pre-moistened toilet wipes, and massage products, among others.

Compositions of the invention may be adapted for inclusion in specific end-use formulations by, for example, mixing or dispersing the active ingredients in selected proportions with a liquid vehicle, provided that the vehicle does not materially affect the antimicrobial efficacy of the compositions.

The vehicle may contain for example, a diluent, an emulsifier, an anti-foam agent, or a wetting-agent; provided that the diluent, the emulsifier, the anti-foam agent, and the wetting-agent do not materially affect the three-component antimicrobial efficacy of the compositions. The compositions of the invention may be provided in liquid mixtures such as dispersions, emulsions, microemulsions, or any other suitable form, provided that additional material which is present in a composition does not materially affect the antimicrobial efficacy of the inventive composition.

End-use formulations for specific applications, may include the inventive composition and, additionally, conventional adjuvants such as surfactants, cleansing agents, and emulsifiers; humectants such as polyols like glycerin and natural moisturizing factors like xylitol and amino acids; emollients such as vegetable oils, natural butters, and waxes; occlusive agents such as silicones, and petrolatum; rheology modifiers such as carbomers, polyacrylates, gums, clays and hydroxyethylcellulose; additional preservatives such as isothiazolinones and parabens; chelating agents such as ethylenediaminetetraacetic acid (EDTA) and pentasodium triphosphate; active ingredients such as chamomile, glycolic acid, and Docosahexaenoic acid (DHA); and the like, provided that the adjuvants do not materially affect the antimicrobial efficacy of the inventive composition.

Treating personal care or cosmetic formulations with a composition of the invention can protect them from microbial attack. The protective treatment may involve mixing the composition with other components of the formulation at any step during production, but the composition is most often mixed into the formulation once it is completed or nearly completed. The method includes treating the personal care or cosmetic formulation with an antimicrobially effective amount of a composition that includes levulinic acid, benzoic acid, and sorbic acids or their respective salts.

The following examples are presented to explain the invention, and are not intended to limit the scope of invention in any way. Unless otherwise indicated, all references to parts and percentages are based on weight.

EXAMPLES

Example 1

Challenge Test Method for Quantifying Antibacterial Effectiveness

In order to quantify the relative antibacterial effectiveness of antimicrobial compositions, samples are prepared by adding known amounts of the compositions to identical volumes of a sterile, preservative-free test material. The test material may be, for example, a shampoo or a body cream. Each of the samples is subjected to the challenge test method and a Bacterial Performance Rating ("BPR") is assigned to each sample based on observations of its bacterial growth under carefully controlled conditions.

Each of the samples is inoculated with a mixed bacterial inoculum as the contamination event. The bacteria in the mixed inoculum are *Pseudomonas aeruginosa* (ATCC #10145), *Escherichia coli* (ATCC #11229), *Enterobacter aerogenes* (ATCC #13048), *Alcaligenes faecalis* (ATCC #25094), and *Staphylococcus aureus* (ATCC 6538).

The antibacterial challenge includes a 168 hour growth cycle, measured from a first contamination in which mixed inoculum is stirred into each of the test samples. The test samples are maintained at room temperature for 48 hours, portions of the test samples are streaked on agar plates, and the samples are again contaminated. The test samples are streaked again at 96 hours, and streaked again at 168 hours.

Antibacterial protection is rated by the level of bacterial growth observed on the agar plate streaked at 168 hours. Even if a sample exhibits more or less bacterial growth earlier in the growth cycle, it is the final reading at the end of seven test days that determines BPR for the sample.

Performance ratings of 0, 1, 2, 3 or 4 for each test sample are determined by visual inspection of the final agar plate according to the definitions set forth below in Table 1.

TABLE 1

| Bacterial Performance Rating (BPR) | Definition |
| --- | --- |
| 0 | No bacterial growth |
| 1 | 1-10 Colonies |
| 2 | 10-100 Colonies |
| 3 | 100-1000 Colonies |
| 4 | >1,000 Colonies |

Example 2

Challenge Method for Quantifying Antifungal Effectiveness

In order to quantify the relative antifungal effectiveness of antimicrobial compositions, samples are prepared by adding known amounts of the compositions to identical volumes of a sterile, preservative-free test material. The test material may be, for example, a shampoo or a body cream. Each of the samples is subjected to the challenge test method and a Fungal Performance Rating ("FPR") is assigned to each sample based on observations of its fungal growth under carefully controlled conditions.

Each of the samples is inoculated with a mixed fungal inoculum as the contamination event. The fungi in the mixed inoculum are *Aspergillus niger* (ATCC #6275) and *Penicillium* sp. (ATCC #12667). The antifungal challenge includes a 168 hour growth cycle, measured from a first contamination in which mixed inoculum is stirred into each of the test samples. The test samples are maintained at room temperature for 48 hours, portions of the test samples are streaked on agar plates, and the samples are again contaminated. The test samples are streaked again at 96 hours, and streaked again at 168 hours.

Antifungal protection is rated by the level of fungal growth observed on the agar plate streaked at 168 hours. Even if a sample exhibits more or less fungal growth earlier in the growth cycle, it is the final reading at the end of seven test days that determines FPR for the sample.

Performance ratings of 0, 1, 2, 3 or 4 for each test sample are determined by visual inspection of the final agar plate according to the definitions set forth below in Table 2.

TABLE 2

| Fungal Performance Rating (BPR) | Definition |
| --- | --- |
| 0 | No fungal growth |
| 1 | 1-10 Colonies |
| 2 | 10-100 Colonies |
| 3 | 100-1,000 Colonies |
| 4 | >1,000 Colonies |

Example 3

Antimicrobial Performance in Shampoo

The Antibacterial Challenge Method described above in Example 1 and the Antifungal Challenge Method described above in Example 2 are performed on shampoo samples which include no preservative and on otherwise identical shampoo samples which include known amounts of levulinic acid, benzoic acid, and/or sorbic acid. In all cases, the shampoo formulations are adjusted to 5.5 pH by addition of sodium hydroxide. The shampoo samples which include no preservative have the composition presented below in Table 3.

TABLE 3

Composition of Shampoo without Preservative

| Component | INCI Name | weight percent |
| --- | --- | --- |
| Water | Water | 82.50 |
| Stepanol WA-Extra HP | Sodium lauryl sulfate | 7.50 |
| Steol CS270 (70%) | Sodium Laureth Sulphate | 7.50 |
| Ninol COMF-N | Cocamide Monoethanol Amine | 2.50 |

Challenge results for shampoo formulations controlled at pH 5.5 are reported in below in Table 4.

TABLE 4

Bacterial and Fungal Performance Ratings for Shampoo Formulations

| Trial No. | LA:BA:SA weight ratio | Preservative Use Level (percent) | Bactericidal Performance Rating (BPR) | | | Fungicidal Performance Rating (FBR) | | |
|---|---|---|---|---|---|---|---|---|
| | | | 48 hours | 96 hours | 168 hours | 48 hours | 96 hours | 168 hours |
| 1 | 0:0:0 | Control | 3 | 4 | 4 | 4 | 4 | 4 |
| 2 | 85:15:0 | 0.40 | 1 | 1 | 1 | 4 | 4 | 4 |
| 3 | 85:15:0 | 0.60 | 1 | 1 | 1 | 3 | 3 | 3 |
| 4 | 85:15:0 | 0.80 | 1 | 1 | 0 | 2 | 2 | 2 |
| 5 | 85:15:0 | 1.00 | 1 | 0 | 0 | 2 | 1 | 1 |
| 6 | 80:15:5 | 0.40 | 2 | 1 | 0 | 4 | 3 | 3 |
| 7 | 80:15:5 | 0.60 | 0 | 0 | 0 | 2 | 2 | 2 |
| 8 | 80:15:5 | 0.80 | 0 | 0 | 0 | 2 | 1 | 1 |
| 9 | 80:15:5 | 1.00 | 0 | 0 | 0 | 1 | 1 | 1 |

Legend:
LA means Levulinic Acid.
BA means Benzoic Acid.
SA means Sorbic Acid.
BPR means Bacterial Performance Rating (described in Table 1 above).
FPR means Fungal Performance Rating (described in Table 2 above).

The data in Table 4 demonstrates that sorbic acid surprisingly reduces the amount of levulinic acid required for bacterial control in shampoo formulations controlled at pH 5.5.

Additionally, the data in Table 4 indicates that a mixture containing 80 percent levulinic acid, 15 percent benzoic acid, and 5 percent sorbic acid protects shampoo formulations controlled at pH 5.5 against bacterial growth after seven days of exposure to contamination at use levels as low as 0.4 percent. These use levels compare favorably to the use level of 0.8 percent which was required when sorbic acid was not included.

Example 4

Antimicrobial Performance of in Body Cream

The Antibacterial Challenge Method described above in Example 1 and the Antifungal Challenge Method described above in Example 2 are performed on body cream samples which include no preservative and on otherwise identical body cream samples which include known amounts of levulinic acid, benzoic acid, and/or sorbic acid. In all cases, the body cream formulations are adjusted to 5.5 pH by addition of sodium hydroxide. The body cream samples which include no preservative have the composition presented below in Table 5.

TABLE 5

Composition of Body Cream With No Preservative

| Component | INCI Name | weight percent |
|---|---|---|
| Water | Water | 74.88 |
| Carbopol Ultrez 20 Polymer | Acrylates/C10-30 Alkyl Acrylate Crosspolymer | 0.30 |
| Glycerine | Glycerine | 3.00 |
| Schecemol 1818 | Isostearyl Isostearate | 7.00 |
| Sheasoft | *Butyrospermum Parkii* (Shea Butter) | 2.00 |
| Grapeseed Oil | *Vitis Vinifera* (Grape) Seed Oil | 5.00 |
| Glucamate SSE-20 | Peg-20 Methyl Glucose Sesquistearate | 2.50 |
| Glucate SS | Methyl Glucose Sesquistearate | 0.80 |
| Hallstar TA-1618 | Cetearyl Alcohol | 1.50 |

Challenge results for body cream formulations controlled at pH 5.5 are reported in below in Table 6.

TABLE 6

Comparison of Antimicrobial Efficacy of Body Cream Formulations

| Trial No. | LA:BA:SA weight ratio | Preservative Use Level (percent) | Bactericidal Performance Rating (BPR) | | | Fungicidal Performance Rating (FPR) | | |
|---|---|---|---|---|---|---|---|---|
| | | | 48 hours | 96 hours | 168 hours | 48 hours | 96 hours | 168 hours |
| 1 | 0:0:0 | Control | 3 | 3 | 3 | 4 | 4 | 4 |
| 2 | 85:15:0 | 0.40 | 2 | 2 | 3 | 4 | 4 | 3 |
| 3 | 85:15:0 | 0.60 | 2 | 2 | 3 | 4 | 3 | 3 |
| 4 | 85:15:0 | 0.80 | 3 | 2 | 1 | 4 | 3 | 3 |
| 5 | 85:15:0 | 1.00 | 2 | 2 | 0 | 4 | 3 | 2 |
| 6 | 80:15:5 | 0.40 | 2 | 2 | 2 | 4 | 4 | 2 |
| 7 | 80:15:5 | 0.60 | 2 | 1 | 0 | 4 | 3 | 2 |
| 8 | 80:15:5 | 0.80 | 1 | 1 | 0 | 3 | 2 | 2 |
| 9 | 80:15:5 | 1.00 | 1 | 0 | 0 | 3 | 2 | 1 |

Legend:
LA means Levulinic Acid.
BA means Benzoic Acid.
SA means Sorbic Acid.
BPR means Bacterial Performance Rating (described in Table 1).
FPR means Fungal Performance Rating (described in Table 2).

The data in Table 6 demonstrates that sorbic acid surprisingly reduces the amount of levulinic acid required for bacterial control in body cream formulations controlled at pH 5.5.

Additionally, the data in Table 6 indicates that a mixture containing 80 percent levulinic acid, 15 percent benzoic acid, and 5 percent sorbic acid protects body cream against bacterial growth after seven days of exposure to contamination at use levels as low as 0.6 percent. These use levels compare favorably to the use levels when required when sorbic acid was not included.

Example 5

Efficacy of Levulinic Acid, Benzoic Acid, and Sorbic Mixtures Acid above 4.5 pH when Combined with Phenylpropanol As noted above, most organic acids exhibit their greatest antimicrobial efficacy at pH of 4.5 or less and suffer a significant loss of efficacy as pH increases to 5.0 and above. While conventional organic acid mixtures are acceptable for many personal care and cosmetic products, there are a number of applications which require a relatively high preservative efficacy at 5.0 pH and above. The inventors were surprised to discover that addition of phenylpropanol to a mixture of levulinic, acid, sorbic acid, and benzoic acid resulted in a significant increase in antimicrobial efficacy at pH greater than 4.5.

The data below in Table 7 demonstrates a pH-related antimicrobial efficacy improvement against both bacteria and fungi. The challenge bacteria were a combination of *Alcaligenes faecalis* (ATCC #25094), *Enterobacter aerogenes* (ATCC #13048), *Escherichia coli* (ATCC #11229), and *Pseudomonas aeruginosa* (ATCC #10145). The challenge fungi were *Aspergillus niger* (ATCC #6275) and *Penicillium* sp. (ATCC #12667).

Samples No. 4 through 15 contained Preservative A, which is a mixture of levulinic acid, benzoic acid, and sorbic acid. The efficacies exhibited by Preservative A at pH levels 4.5, 5.5, and 6.5 and at use levels of 0.4, 0.6, 0.8, and 1.0 percent are presented in Table 7.

The efficacies exhibited at these same conditions by Samples No. 16 through 27 contained Preservative B; which is a mixture of phenylpropanol, levulinic acid, benzoic acid, and sorbic acid; are also presented below in Table 7.

TABLE 7

Augmented Efficacy in Wet Wipes above 4.5 pH (Phenylpropanol)

| | | | | Bacteria | | | | Fungi | | | |
|---|---|---|---|---|---|---|---|---|---|---|---|
| Sample No. | pH | Preservative | Use Level | 2 days | 4 days | 7 days | 14 days | 2 days | 4 days | 7 days | 14 days |
| 1 | 4.5 | None | None | 2 | 3 | 3 | 3 | 4 | 4 | 4 | 4 |
| 2 | 5.5 | None | None | 4 | 3 | 3 | 4 | 4 | 4 | 4 | 3 |
| 3 | 6.5 | None | None | 4 | 4 | 4 | 4 | 4 | 4 | 4 | 4 |
| 4 | 4.5 | A# | 0.40% | 0 | 0 | 0 | 0 | 3 | 2 | 2 | 2 |
| 5 | 4.5 | A | 0.60% | 0 | 0 | 0 | 0 | 2 | 1 | 0 | 1 |
| 6 | 4.5 | A | 0.80% | 0 | 0 | 0 | 0 | 2 | 0 | 0 | 0 |
| 7 | 4.5 | A | 1.00% | 0 | 0 | 0 | 0 | 2 | 0 | 0 | 0 |
| 8 | 5A | A | 0.40% | 3 | 2 | 1 | 0 | 4 | 4 | 3 | 3 |
| 9 | 5.5 | A | 0.60% | 3 | 3 | 1 | 0 | 4 | 4 | 3 | 3 |
| 10 | 5.5 | A | 0.80% | 3 | 2 | 0 | 0 | 3 | 3 | 3 | 2 |
| 11 | 5.5 | A | 1.00% | 3 | 3 | 1 | 0 | 4 | 4 | 3 | 2 |
| 12 | 6.5 | A | 0.40% | 4 | 4 | 4 | 4 | 4 | 4 | 3 | 3 |
| 13 | 6.5 | A | 0.60% | 4 | 4 | 4 | 4 | 4 | 4 | 3 | 3 |
| 14 | 6.5 | A | 0.80% | 4 | 4 | 4 | 3 | 4 | 3 | 3 | 3 |
| 15 | 6.5 | A | 1.00% | 4 | 4 | 4 | 4 | 4 | 3 | 3 | 3 |
| 16 | 4.5 | B^ | 0.40% | 0 | 0 | 0 | 0 | 2 | 1 | 0 | 2 |
| 17 | 4.5 | B | 0.60% | 0 | 0 | 0 | 0 | 2 | 1 | 1 | 0 |
| 18 | 4.5 | B | 0.80% | 0 | 0 | 0 | 0 | 2 | 0 | 0 | 1 |
| 19 | 4.5 | B | 1.00% | 0 | 0 | 0 | 0 | 1 | 0 | 0 | 0 |
| 20 | 5.5 | B | 0.40% | 1 | 0 | 0 | 0 | 3 | 2 | 2 | 2 |
| 21 | 5.5 | B | 0.60% | 0 | 0 | 0 | 0 | 3 | 1 | 1 | 1 |
| 22 | 5.5 | B | 0.80% | 0 | 0 | 0 | 0 | 2 | 0 | 0 | 0 |
| 23 | 5.5 | B | 1.00% | 0 | 0 | 0 | 0 | 2 | 0 | 0 | 0 |
| 24 | 6.5 | B | 0.40% | 4 | 1 | 0 | 0 | 3 | 2 | 1 | 1 |
| 25 | 6.5 | B | 0.60% | 1 | 0 | 0 | 0 | 3 | 1 | 1 | 0 |
| 26 | 6.5 | B | 0.80% | 0 | 0 | 0 | 0 | 1 | 0 | 0 | 0 |
| 27 | 6.5 | B | 1.00% | 0 | 0 | 0 | 0 | 1 | 0 | 0 | 0 |

Legend:
Preservative A includes 40% levulinic acid, 5% sorbic acid, and 15% benzoic acid.
^Preservative B includes 40% levulinic acid, 5% sorbic acid, 15% benzoic acid and 40% phenylpropanol The data in Table 7 indicate that Preservative A and Preservative B performed similarly at pH 4.5, a level of acidity at which conventional organic acids are highly effective. As the pH increased to 5.5 and 6.5, the antimicrobial performance of the two systems diverged significantly, with Preservative B (containing phenylpropanol) continuing to show excellent microefficacy against both bacteria and fungi at the higher pH. This is a surprising result considering that phenylpropanol is usually employed to inhibit bacteria, rather than fungi. Also, the lowest use levels reported for Preservative B in Table 7 (specifically, 0.4%) correspond to a relatively low concentration of phenylpropanol that would not be expected to contribute significantly to antibacterial efficacy or antifungal efficacy.

The data in Table 7 demonstrates that phenylpropanol extended the effective pH range of an organic acid preservative mixture for preserving wet wipes.

Example 6

Efficacy of Levulinic Acid, Benzoic Acid, and Sorbic Mixtures Acid above 4.5 pH when Combined with Phenoxyethanol The inventors have discovered that the presence of phenoxyethanol, when present in a mixture of levulinic acid, sorbic acid, and benzoic alcohol, produces a significant increase in antimicrobial efficacy at pH greater than 4.5.

Data presented below in Table 8 below demonstrates a pH-related efficacy improvement observed in wet wipes when organic acids were augmented by phenoxyethanol. Samples No. 4 through 15, containing Preservative A, were described above with regard to Table 7 as being a mixture of levulinic acid, benzoic acid, and sorbic acid. The efficacies of Preservative A at pH levels of 4.5, 5.5, and 6.5 and at use levels of 0.4, 0.6, 0.8, and 1.0 percent against bacteria and fungi are again presented in Table 8 for ease of comparison. Samples No. 1 through 3 were control samples that contained no preservatives.

The benefits of augmentation with phenoxyethanol are apparent in Samples No. 28 through 39 ("Preservative C"), which is a mixture of phenoxyethanol, levulinic acid, benzoic acid, and sorbic acid. The efficacies exhibited by Preservative C at pH levels of 4.5, 5.5, and 6.5 and at use levels of 0.4, 0.6, 0.8, and 1.0 percent against bacteria and fungi are also presented below in Table 8.

TABLE 8

Augmented Efficacy in Wet Wipes above 4.5 pH (Phenoxyethanol)

| | | | Bacteria | | | | Fungi | | | |
|---|---|---|---|---|---|---|---|---|---|---|
| Sample No. | pH | Preservative | Use Level | 2 days | 4 days | 7 days | 14 days | 2 days | 4 days | 7 days | 14 days |
| 1 | 4.5 | None | None | 2 | 3 | 3 | 3 | 4 | 4 | 4 | 4 |
| 2 | 5.5 | None | None | 4 | 3 | 3 | 4 | 4 | 4 | 4 | 3 |
| 3 | 6.5 | None | None | 4 | 4 | 4 | 4 | 4 | 4 | 4 | 4 |
| 4 | 4.5 | A# | 0.40% | 0 | 0 | 0 | 0 | 3 | 2 | 2 | 2 |
| 5 | 4.5 | A | 0.60% | 0 | 0 | 0 | 0 | 2 | 1 | 0 | 1 |
| 6 | 4.5 | A | 0.80% | 0 | 0 | 0 | 0 | 2 | 0 | 0 | 0 |
| 7 | 4.5 | A | 1.00% | 0 | 0 | 0 | 0 | 2 | 0 | 0 | 0 |
| 8 | 5A | A | 0.40% | 3 | 2 | 1 | 0 | 4 | 4 | 3 | 3 |
| 9 | 5.5 | A | 0.60% | 3 | 3 | 1 | 0 | 4 | 4 | 3 | 3 |
| 10 | 5.5 | A | 0.80% | 3 | 2 | 0 | 0 | 3 | 3 | 3 | 2 |
| 11 | 5.5 | A | 1.00% | 3 | 3 | 1 | 0 | 4 | 4 | 3 | 2 |
| 12 | 6.5 | A | 0.40% | 4 | 4 | 4 | 4 | 4 | 4 | 3 | 3 |
| 13 | 6.5 | A | 0.60% | 4 | 4 | 4 | 4 | 4 | 4 | 3 | 3 |
| 14 | 6.5 | A | 0.80% | 4 | 4 | 4 | 3 | 4 | 3 | 3 | 3 |
| 15 | 6.5 | A | 1.00% | 4 | 4 | 4 | 4 | 4 | 3 | 3 | 3 |
| 28 | 4.5 | C= | 0.40% | 0 | 0 | 0 | 0 | 2 | 1 | 0 | 2 |
| 29 | 4.5 | C | 0.60% | 0 | 0 | 0 | 0 | 2 | 1 | 1 | 0 |
| 30 | 4.5 | C | 0.80% | 0 | 0 | 0 | 0 | 2 | 0 | 0 | 1 |
| 31 | 4.5 | C | 1.00% | 0 | 0 | 0 | 0 | 1 | 0 | 0 | 0 |
| 32 | 5.5 | C | 0.40% | 1 | 0 | 0 | 0 | 3 | 2 | 2 | 2 |
| 33 | 5.5 | C | 0.60% | 0 | 0 | 0 | 0 | 3 | 1 | 1 | 1 |
| 34 | 5.5 | C | 0.80% | 0 | 0 | 0 | 0 | 2 | 0 | 0 | 0 |
| 35 | 5.5 | C | 1.00% | 0 | 0 | 0 | 0 | 2 | 0 | 0 | 0 |
| 36 | 6.5 | C | 0.40% | 4 | 1 | 0 | 0 | 3 | 2 | 1 | 1 |
| 37 | 6.5 | C | 0.60% | 1 | 0 | 0 | 0 | 3 | 1 | 1 | 0 |
| 38 | 6.5 | C | 0.80% | 0 | 0 | 0 | 0 | 1 | 0 | 0 | 0 |
| 39 | 6.5 | C | 1.00% | 0 | 0 | 0 | 0 | 1 | 0 | 0 | 0 |

Legend:
Preservative A includes 40% levulinic acid, 5% sorbic acid, and 15% benzoic acid.
=Preservative C includes 40% levulinic acid, 5% sorbic acid, 15% benzoic acid, and 40% Phenoxyethanol.

The data in Table 8 indicate that Preservative A and Preservative C perform similarly at pH 4.5. As the pH was increased to 5.5 and 6.5, the antimicrobial performance of the two systems diverged significantly, with Preservative C (containing phenoxyethanol) exhibiting excellent efficacy against both bacteria and fungi at the higher pH. This is a surprising result considering that phenoxyethanol is usually employed against bacteria, rather than fungi. Also, the lowest use levels reported for Preservative C in Table 8 (specifically, 0.4%) correspond to a relatively low concentration of phenoxyethanol that would not be expected to contribute significantly to antibacterial efficacy or antifungal efficacy.

The data in Table 8 demonstrates that phenoxyethanol extended the effective pH range of an organic acid preservative mixture for preserving wet wipes.

Example 7

Stability of Levulinic Acid and Phenoxyethanol Mixture

In order to demonstrate that a mixture of levulinic acid and phenoxyethanol is sufficiently stable for use in the Personal care industry, an equal parts mixture of levulinic acid and phenoxyethanol was prepared at room temperature and a portion of the mixture was immediately analyzed by Horizontal Attenuated Total Reflectance-Fourier Transform Infra Red Spectroscopy (also known as HATR-FTIR). The immediate results are depicted by a solid-line trace in FIG. 1 which presents absorbance (dimensionless) as a function of wave number (1/cm).

Another portion of the mixture was stored at 50 degrees C. for seven days and then analyzed by HATR-FTIR. The seven day results are depicted as a dashed-line trace in FIG. 1 which presents absorbance as a function of wave number.

Figure 1:
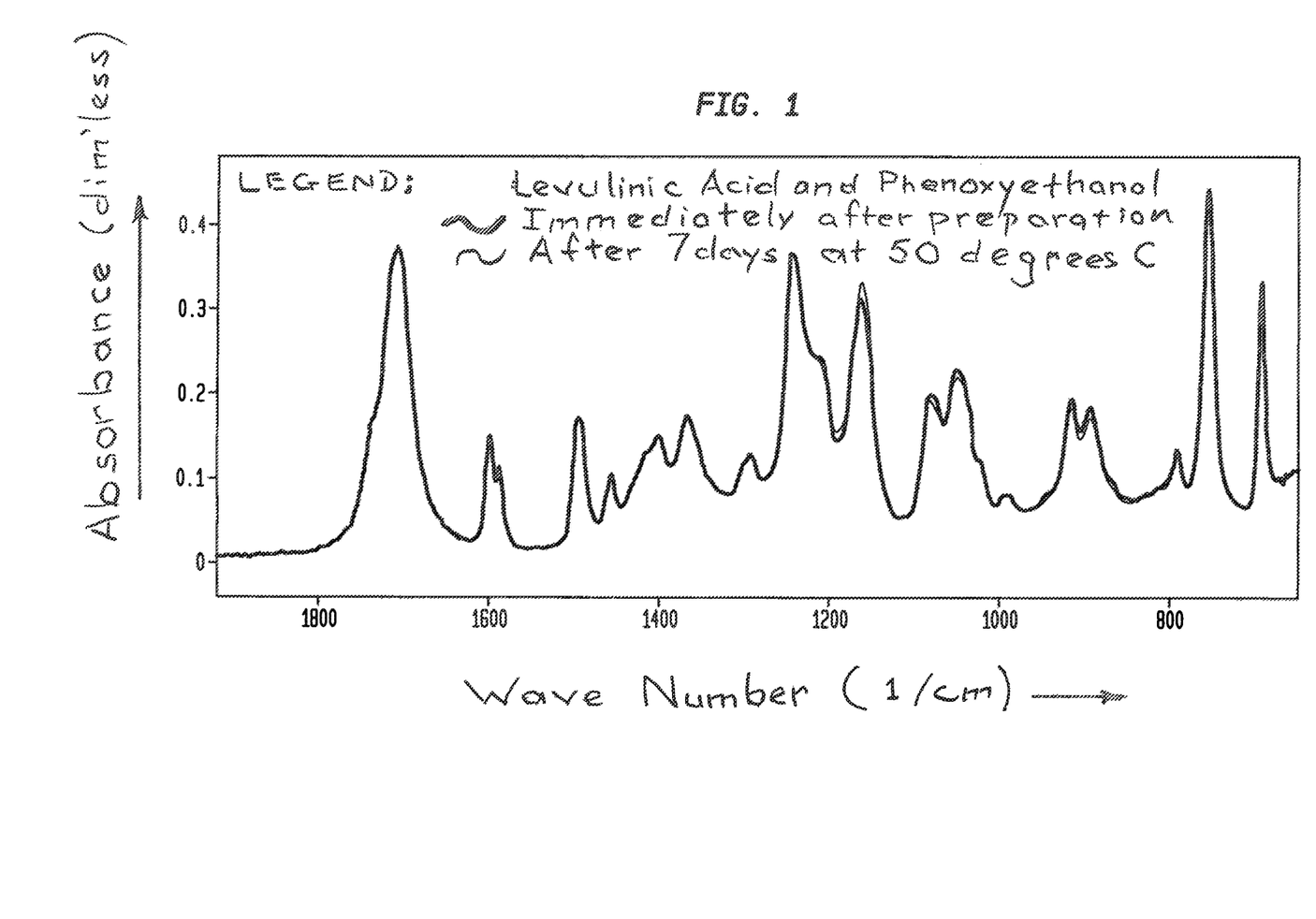
FIG. 1 is a graph depicting absorbance as a function of wave number for Horizontal Attenuated Total Reflectance-Fourier Transform Infra Red Spectroscopy results of two samples containing levulinic acid and phenoxyethanol.

Inspection of FIG. 1 reveals no significant difference between the immediate, room temperature sample and the seven day, 50 degree C. sample. Based on these results, the mixture of levulinic acid and phenoxyethanol is sufficiently stable for commercial.

Example 8

Stability of Levulinic Acid and Benzyl Alcohol Mixture

In order to demonstrate that a mixture of levulinic acid and benzyl alcohol is sufficiently stable for use in the Personal Care industry, an equal parts mixture of levulinic acid and benzyl alcohol was prepared at room temperature and a portion of the mixture was immediately analyzed by Horizontal Attenuated Total Reflectance-Fourier Transform Infra Red Spectroscopy (also known as HATR-FTIR). The immediate results are depicted by a solid-line trace in FIG. 1, which presents absorbance (dimensionless) as a function of wave number (1/cm).

Another portion of the mixture was stored at 50 degrees C. for seven days and then analyzed by HATR-FTIR. The seven day results are depicted as a dashed-line trace in FIG. 2, which depicts absorbance as a function of wave number.

Figure 2:
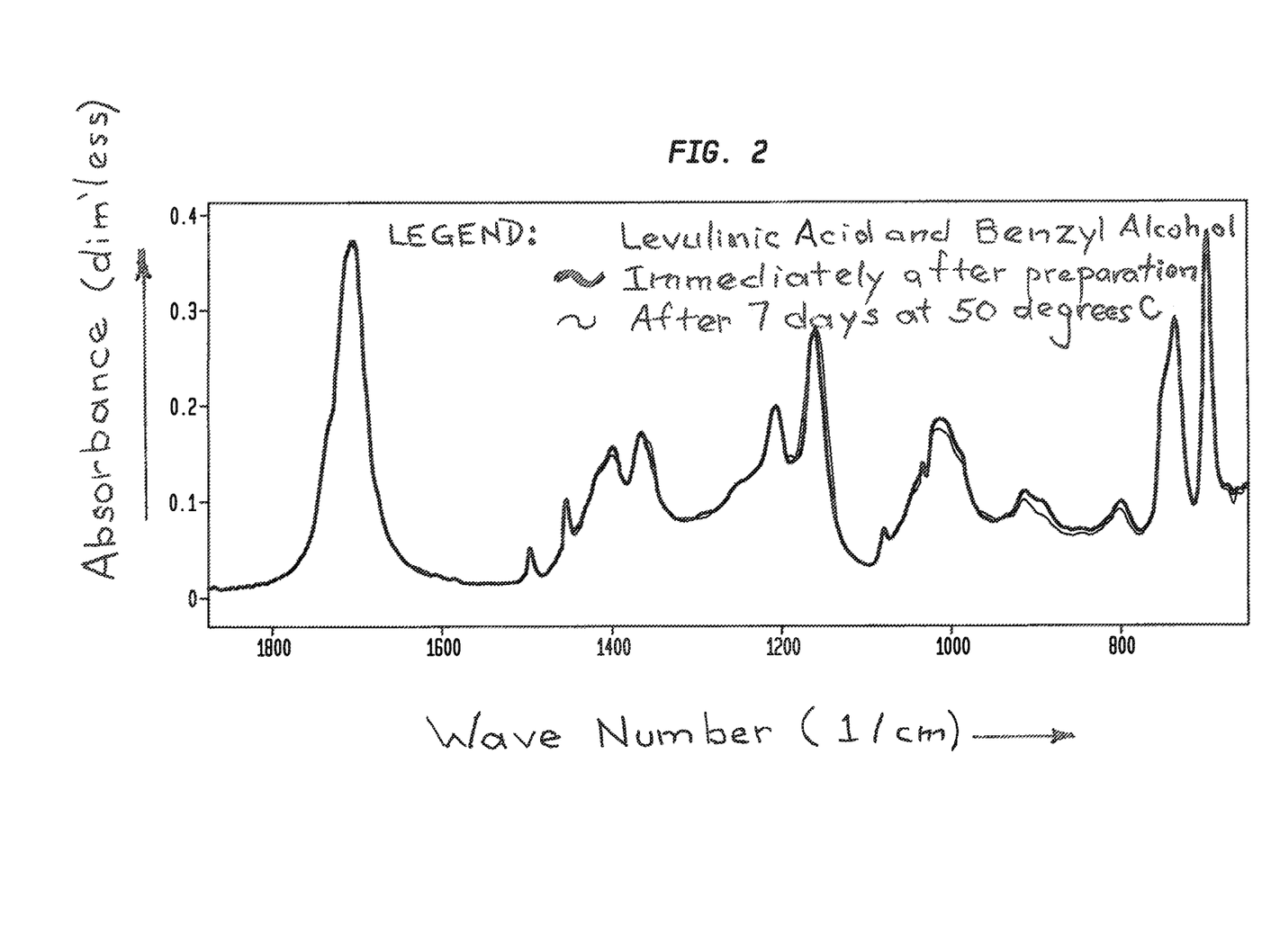
FIG. 2 is a graph depicting absorbance as a function of wave number for Horizontal Attenuated Total Reflectance-Fourier Transform Infra Red Spectroscopy results of two samples containing levulinic acid and benzyl alcohol.

Inspection of FIG. 2 reveals no significant or measurable difference between the immediate, room temperature sample and the seven day, 50 degree C. sample. Based on these results, the mixture of levulinic acid and benzyl alcohol is sufficiently stable for use in the Personal Care industry.

Example 9

MIC of Levulinic Acid, Benzoic Acid, and Sorbic Acid Mixtures against Bacteria

Microdilution plates having wells of 200 microliter capacity, and the materials in Table 9 are used to determine Minimum Inhibitory Concentration ("MIC") of two preservative compositions of the invention and of one comparison composition against the bacteria *Pseudomonas aeruginosa*, *Escherichia coli*, and *Staphylococcus aureus*.

TABLE 9

| Materials |
| --- |
| 2X Nutrient Broth adjusted to pH 5.0 |
| Sterile water at pH 5.5 |
| 50% solution of Sodium Hydroxide (NaOH) |
| 4% dilution stock solution |
| 96-well microdilution plates |
| *Pseudomonas aeruginosa* (ATCC 9027) |
| *Escherichia coli* (ATCC 8739) |
| *Staphylococcus aureus* (ATCC 6538) |

Each of the three compositions is diluted with sterile water to 4.0% and adjusted to 5.0 pH with 50% aqueous sodium hydroxide to produce three 4% working stock solutions. Each of three bacterial inoculums is diluted with sterile water to produce three working cultures of 5.0×104 colony-forming units per milliliter (CFU/mL). Thirty-two of the wells are charged with 100 microliters of sterile water and 100 microliters of the 4% working stock used in serial two fold dilution to obtain 2.0%, 1.0% and 0.5% and 0.25% concentration test wells in eight replicates.

Other wells are utilized as controls. Negative controls consist of water mixed with 4% solution. Quality controls consist of sterile buffered water with 4% working stock solution. Positive controls consist of nutrient broth with one of the bacteria. After inoculation and before incubation, the working culture is used to perform a colony count check of growth in Trypticase Soy Agar.

TABLE 9

MIC against bacteria for Levulinic Acid, Benzoic Acid, and Sorbic Acid mixtures

| | | Minimum Inhibitory Concentration* (percent) | | |
| --- | --- | --- | --- | --- |
| Trial No. | LA:BA:SbA weight ratio | *Pseudomonas aeruginosa* | *Escherichia coli* | *Staphylococcus aureus* |
| 1 | 85:15:0 | 0.5 | 2.0 | 2.0 |
| 2 | 85:12:2.5 | 0.5 | 1.0 | 1.0 |
| 3 | 85:10:5.0 | 1.0 | 0.5 | 0.5 |

Legend:
*Each reported Minimum Inhibitory Concentration is the mean average value of eight replications
LA means levulinic acid.
BA means boric acid.
SA means sorbic acid.

The data in Table 10 indicates that two mixtures of the invention, which contain 85% percent levulinic acid with the balance being benzoic acid and sorbic acid, exhibit a lesser MIC against *Escherichia coli* and *Staphylococcus aureus* than is exhibited by a binary solution not of the invention consisting of 85% levulinic acid and 15% benzoic acid. No decrease in MIC is observed against *Pseudomonas aeruginosa* over this range.

We claim as our invention:

1. An antibacterial and antifungal preservative composition, comprising:
   (a) levulinic acid or a salt thereof;
   (b) benzoic acid or a salt thereof; and
   (c) sorbic acid or a salt thereof,
   wherein (a), (b), and (c) are present in a weight ratio (a):(b):(c) of 80:15:5.

2. The composition of claim 1, further comprising an aromatic alcohol.

3. The composition of claim 2, in which the aromatic alcohol is selected from the group consisting of phenoxyethanol, phenylpropanol, phenylethanol, benzyl alcohol, and mixtures thereof.

4. The composition of claim 3, in which the aromatic alcohol is selected from the group consisting of phenoxyethanol, phenylpropanol, and mixtures thereof.

5. The composition of claim 1, which includes an aqueous solvent.

6. An antibacterial and antifungal preservative composition, comprising:
   (a) levulinic acid or a salt thereof;
   (b) benzoic acid or a salt thereof;
   (c) sorbic acid or a salt thereof; and
   (d) an aromatic alcohol,
   wherein (a), (b), (c), and (d) are present in a weight ratio (a):(b):(c):(d) of 40:15:5:40.

7. The composition of claim 6, in which the aromatic alcohol is selected from the group consisting of phenoxyethanol, phenylpropanol, phenylethanol, benzyl alcohol and mixtures thereof.

8. The composition of claim 7, which includes phenoxyethanol, phenylpropanol, and mixtures thereof.

9. A personal care or cosmetic product, having a pH in the range of 4.5 pH to 7.0 pH and comprising a liquid vehicle and 0.2% to 2.0% by weight of the composition of claim 1.

10. The personal care or cosmetic product of claim 9, comprising 0.1% to 1.0% by weight of the composition of claim 1.

11. The personal care or cosmetic composition of claim 9, having a pH in the range of 4.5 pH to 6.5 pH.

12. The personal care or cosmetic composition of claim 9, having a pH in the range of 5.5 pH to 6.5 pH.

13. A method of protecting a personal care or cosmetic formulation from microbial attack, comprising adding to a personal care or cosmetic formulation comprising a liquid vehicle and having a pH in the range of 4.5 pH to 7.0 pH an antimicrobially effective amount of an antibacterial and antifungal preservative composition, said preservative composition comprising:
   (a) levulinic acid or a salt thereof;
   (b) benzoic acid or a salt thereof; and
   (c) sorbic acid or a salt thereof,
   wherein (a), (b), and (c) are present in a weight ratio (a):(b):(c) of 80:15:5.

14. The method of claim 13, wherein the preservative composition is added to the personal care or cosmetic formulation in an amount of 0.2% to 4.0% by weight of the personal care or cosmetic formulation.

15. The method of claim 14, wherein the preservative composition is added to the personal care or cosmetic formulation in an amount of 0.4% to 1.0% by weight of the personal care or cosmetic formulation.

16. A method of protecting a personal care or cosmetic formulation from microbial attack, comprising adding to a personal care or cosmetic formulation comprising a liquid vehicle and having a pH in the range of 4.5 pH to 7.0 pH an antimicrobially effective amount of an antibacterial and antifungal preservative composition, said preservative composition comprising:
   (a) levulinic acid or a salt thereof;
   (b) benzoic acid or a salt thereof;
   (c) sorbic acid or a salt thereof; and
   (d) an aromatic alcohol,
   wherein (a), (b), (c), and (d) are present in a weight ratio (a):(b):(c):(d) of 40:15:5:40.

17. The method of claim 16, wherein the preservative composition is added to the personal care or cosmetic formulation in an amount of 0.2% to 4.0% by weight of the personal care or cosmetic formulation.

18. The method of claim 17, wherein the preservative composition is added to the personal care or cosmetic formulation in an amount of 0.4% to 1.0% by weight of the personal care or cosmetic formulation.

* * * * *

UNITED STATES PATENT AND TRADEMARK OFFICE
CERTIFICATE OF CORRECTION

PATENT NO. : 11,122,800 B2
APPLICATION NO. : 15/799998
DATED : September 21, 2021
INVENTOR(S) : David Joseph Koehl It is certified that error appears in the above-identified patent and that said Letters Patent is hereby corrected as shown below:

In the Specification

In Column 14, Example 9, Line 44, "TABLE 9" should read -- TABLE 10 --

In Column 14, Example 9, Line 58, "BA means boric acid" should read -- BA means benzoic acid --

Signed and Sealed this
Twenty-second Day of March, 2022

Drew Hirshfeld
*Performing the Functions and Duties of the*
*Under Secretary of Commerce for Intellectual Property and*
*Director of the United States Patent and Trademark Office*